United States Patent
Nikolayev et al.

(10) Patent No.: US 11,616,290 B2
(45) Date of Patent: *Mar. 28, 2023

(54) MULTI-BAND LOW PROFILE RADIO ANTENNA

(71) Applicants: BODYCAP, Herouvile Saint Clair (FR); CENTRE NATIONAL DE LA RECHERCHE SCIENTIFIQUE, Paris (FR); UNIVERSITE DE RENNES 1, Rennes (FR)

(72) Inventors: Denys Nikolayev, Rennes (FR); Maxim Zhadobov, Betton (FR); Ronan Sauleau, Acigné (FR)

(73) Assignees: BODYCAP, Herouvile Saint Clair (FR); CENTRE NATIONAL DE LA RECHERCHE SCIENTIFIQUE, Paris (FR); UNIVERSITE DE RENNES 1, Rennes (FR)

(*) Notice: Subject to any disclaimer, the term of this patent is extended or adjusted under 35 U.S.C. 154(b) by 0 days.

This patent is subject to a terminal disclaimer.

(21) Appl. No.: 17/571,326

(22) Filed: Jan. 7, 2022

(65) Prior Publication Data

US 2022/0209394 A1 Jun. 30, 2022

Related U.S. Application Data

(63) Continuation of application No. 16/652,276, filed as application No. PCT/FR2018/052444 on Oct. 4, 2018, now Pat. No. 11,258,166.

(30) Foreign Application Priority Data

Oct. 4, 2017 (FR) .................................. FR1759268

(51) Int. Cl.
*H01Q 1/38* (2006.01)
*H01Q 1/27* (2006.01)
(Continued)

(52) U.S. Cl.
CPC ............. *H01Q 1/273* (2013.01); *A61B 5/073* (2013.01); *H01Q 1/38* (2013.01); *H01Q 1/48* (2013.01);
(Continued)

(58) Field of Classification Search
CPC .......... H01Q 21/30; H01Q 21/28; H01Q 1/48; H01Q 1/38; H01Q 5/357; H01Q 1/273
See application file for complete search history.

(56) References Cited

U.S. PATENT DOCUMENTS

| 6,515,629 B1 * | 2/2003 | Kuo .......................... H01Q 1/38 343/702 |
| 2004/0263396 A1 | 12/2004 | Sung |

(Continued)

FOREIGN PATENT DOCUMENTS

| CN | 105870602 | 8/2016 |
| FR | 2703872 | 10/1994 |

(Continued)

OTHER PUBLICATIONS

Search Report dated Dec. 4, 2018 for PCT Application No. PCT/FR2018/052444.

(Continued)

*Primary Examiner* — Graham P Smith

(57) ABSTRACT

Disclosed is a radio antenna comprising a substrate of dielectric material; a ground plane of electrically conductive material on a first face of the substrate; a resonator for converting an incident electrical signal into an electromagnetic wave and for resonating at at least two different resonant frequencies. The resonator comprises at least three elements, each in the form of strips of conductive material and arranged on a second face of the substrate opposite the first face. A second element is electrically connected to the ground plane by means of a via passing through the substrate (Continued)

at a first end of the corresponding strip, forms an extension of the first element, and is electrically connected directly to the first element at a second end of said strip which is opposite the first end.

15 Claims, 7 Drawing Sheets

(51) Int. Cl.
*H01Q 5/357* (2015.01)
*A61B 5/07* (2006.01)
*H01Q 1/48* (2006.01)
*H01Q 21/28* (2006.01)
*H01Q 21/30* (2006.01)

(52) U.S. Cl.
CPC ............. *H01Q 5/357* (2015.01); *H01Q 21/28* (2013.01); *H01Q 21/30* (2013.01); *A61B 2562/162* (2013.01)

(56) References Cited

U.S. PATENT DOCUMENTS

| | | |
|---|---|---|
| 2008/0042916 A1 | 2/2008 | Ma |
| 2010/0149042 A1 | 6/2010 | Utsi et al. |
| 2012/0280885 A1 | 11/2012 | Arai et al. |
| 2014/0152514 A1 | 6/2014 | Vilenskiy et al. |
| 2017/0117620 A1 | 4/2017 | Lapushin |

FOREIGN PATENT DOCUMENTS

| | | |
|---|---|---|
| KR | 20140119606 | 10/2014 |
| WO | WO2011/111008 | 9/2011 |

OTHER PUBLICATIONS

Sumin Yun et al., Outer-Wall Loop Antenna for Ultrawideband Capsule Endoscope System, IEEE Antennas And Wireless Propagation Letters, 2010, pp. 1135-1138, vol. 9.

\* cited by examiner

MULTI-BAND LOW PROFILE RADIO ANTENNA

CROSS-REFERENCE TO RELATED APPLICATION

This application is a continuation application of U.S. patent application Ser. No. 16/652,276 filed Mar. 30, 2020, which is a national stage application, filed under 35 U.S.C. § 371, of International Patent Application No. PCT/FR2018/052444, filed on Oct. 4, 2018, which claims priority of French application No. FR1759268, filed on Oct. 4, 2017, which is incorporated by reference herein in its entirety.

TECHNICAL FIELD

The present description relates to a multi-band radio antenna and a biotelemetry device equipped with such an antenna.

STATE OF THE ART

In the field of medical applications, biotelemetry devices are used for the acquisition of physiological signals and the analysis of associated physiological data.

Among the biometric devices, there are ingestible and/or in vivo implantable biometric devices, which can be used both for collecting physiological signals and the implementation of therapeutic functions, such as for example drug delivery or electrical stimulation. These biotelemetry devices are for example in the form of ingestible capsules or implants which can be inserted into the body of humans or animals.

These biotelemetry devices incorporate a radio antenna configured to transmit and/or receive an electromagnetic wave. The radio antenna is used to transmit data to, or receive instructions from, external data control/analysis equipment. These external equipments are used in particular to analyze ex vivo the data transmitted by the radio antenna.

The performances of the antenna with regard to data transmission and transmission power are highly dependent on the electromagnetic properties of the surrounding environment.

In fact, when the biotelemetry device is placed in a surrounding medium (for example a biological medium), the antenna is strongly coupled with this surrounding medium and the impedance of the radioelectric antenna is thus strongly dependent on the electromagnetic properties (permittivity, conductivity) of this surrounding medium. Thus, an impedance mismatch of the radio antenna with respect to the microcontroller can occur due to the electromagnetic properties of the surrounding medium.

An impedance mismatch between the antenna and the microprocessor in fact induces energy losses in the biotelemetry device and impacts the transmission performance of the antenna, in particular the power of the electromagnetic wave emitted. This is all the more problematic since the electromagnetic wave must, to reach the external equipment, pass through various human or animal biological tissues, which are highly dispersive, which contribute to the low radiation efficiency ($\eta<0.1\%$).

In addition, when the impedance of the antenna is affected by the surrounding medium, this also results in a modification both of the resonance frequency of this antenna and its level of adaptation to the operating frequency, this level of adaptation being characterized by the reflection coefficient $|S_{11}|$ determined as the complex ratio (i.e. determined in amplitude and phase) between the complex intensity of the incident electrical signal converted by the antenna into an electromagnetic wave and the complex intensity of the reflected electrical signal resulting from a reflection of a fraction of the incident electric signal.

One approach to increase the antenna immunity to impedance mismatch is to design a broadband radio antenna, so that the bandwidth covers the frequency range in which the antenna will operate given the expected mismatching effect. However, such an extension of the bandwidth often implies sacrificing the radiation efficiency.

The article entitled "Design, realization and measurements of a miniature antenna for implantable wireless communication Systems", by F. Merli et al., IEEE Transactions Antennas Propagation, vol. 59, n ° 10, pages 3544-3555, October 2011, discloses an example of a multi-band radioelectric antenna, in the form of an helix, having dimensions suitable for subcutaneous implantation (10×32.1 mm) This antenna is however heavy and bulky (it fills about a quarter of the available volume) for integration into a biotelemetry device of the ingestible or implantable capsule type. It is indeed difficult to produce a miniature antenna, suitable for integration into a biotelemetry device, while improving transmission performance.

Thus, there appears a need for a multi-band antenna, robust in impedance and adaptable in impedance for at least two resonance frequencies, which is not very bulky so as to be usable in an ingestible biotelemetry device and/or in vivo implantable.

SUMMARY

The present description relates, according to a first aspect, to a multi-band radio antenna. The radio antenna includes: a substrate formed of a dielectric material; a ground plane of electrically conductive material, arranged on a first face of the substrate; a resonator configured to convert an incident electrical signal into an electromagnetic wave and to resonate at at least two distinct resonant frequencies, the resonator comprising at least three elements arranged on a second face of the substrate opposite the first face. A first element is formed by a first strip of electrically conductive material. A second element is formed by a second strip of electrically conductive material. A third element is formed by a third strip of electrically conductive material. The second element is electrically connected to the ground plane by means of a via passing through the substrate at a first end of the second strip. The second element forms an extension of the first element and is electrically connected directly to the first element at a second end of the second strip opposite the first end. The first element is separated from the third element by a slot and electrically connected to the third element at one end of the first strip and one end of the third strip via a transition strip of electrically conductive material crossing the slot. The third element is connected to a power supply line to receive the incident electrical signal.

In at least one embodiment, the first element and the second element form a quarter-wave resonator with impedance jump, with an impedance transition between the first element and the second element having an impedance greater than that of the first element, and the third element radiates like a half-wave patch antenna.

The radio antenna according to the first aspect uses elements in the form of a strip of electrically conductive material, produced for example, according to the technology known as microstrip.

This multiband microstrip antenna is suitable for multiple in vivo uses by allowing communication (data exchange in particular) with an external device through a lossy medium such as the human body, having variable electromagnetic properties, and at the same time measuring a reflection coefficient.

It can be designed so as to have a given impedance (for example 50Ω), for at least two operating frequencies (or resonance frequencies), for example for the operating frequencies 434 MHz and 2.45 GHz.

This radio antenna is a multi-band antenna, having both a high efficiency and a good robustness in impedance. These characteristics are obtained by decoupling the antenna from the surrounding lossy environment using the specific microstrip design of the antenna. In addition, the antenna can be dielectrically charged by a high permittivity superstrate so as to improve its robustness and its efficiency. The gains that can be obtained are greater than −20 dBi, and the radiation efficiency is in the order of 2% and 1% obtained respectively for the operating frequencies 434 MHz and 2.45 GHz.

By varying the dimensions of the three elements of the resonator, the two resonance frequencies can be adjusted to the intended application cases. Due to the particular configuration of the bands, it is also possible to carry out an impedance matching for the two resonance frequencies of the antenna.

The impedance of the antenna is also not very sensitive to variations in the surrounding environment. The reflection coefficient $S_{11}$ is such that $|S_{11}|<-10$ dB in a range of surrounding environments.

Such an antenna lends itself to being produced in a printed circuit and can also be integrated into a biotelemetry capsule (for example, an ingestible biotelemetry capsule, 28 mm long and 9 mm diameter).

Such a radio antenna is also suitable for making a miniature radio antenna, for example with a substrate thickness of less than 1 mm and a substrate width/length of less than 3 cm, and can therefore easily be integrated into a biotelemetry device such as a biotelemetry capsule. Such an antenna is a low profile antenna ("low profile" according to English terminology), the thickness of the antenna being negligible compared to its size. Such an antenna occupies negligible space in a biotelemetry capsule, allows a high degree of miniaturization while having increased transmission efficiency.

Such a radio antenna can also be produced on a flexible substrate, so as to be able to conform to the interior surface of a biotelemetry device such as a capsule.

In one or more embodiments of the radio antenna according to the first aspect, the first element and the second element are configured to resonate at a first resonance frequency and the third element is configured to resonate at a second resonance frequency greater than the first resonance frequency.

In one or more embodiments of the radio antenna according to the first aspect, the ratio between the width of the first band and the width of the second band is from 2:1 to 100:1.

In one or more embodiments of the radio antenna according to the first aspect, at least one of the first, second, third and fourth bands has a rectangular, coiled or zigzag shape.

In one or more embodiments of the radio antenna according to the first aspect, the thickness of the substrate is 20 µm to 5 mm.

The characteristics of the various embodiments of the radio antenna according to the first aspect can be combined with one another.

The present description relates, according to a second aspect, to a biotelemetry device comprising a radio antenna according to the first aspect. The characteristics, properties, advantages and/or effects of the radio antenna according to the first aspect can be transposed directly to the biotelemetry device according to the second aspect.

In one or more embodiments of the biotelemetry device according to the second aspect, the substrate being in a flexible material and the biotelemetry device being in the form of a capsule in which the substrate is rolled so that the first face of the substrate faces the inside of the capsule and the second face faces the outside of the capsule.

In one or more embodiments of the biotelemetry device according to the second aspect, the substrate of the radio antenna is a flexible polyimide substrate conforming to the internal surface of the capsule.

In one or more embodiments of the biotelemetry device according to the second aspect, the substrate is made of a rigid material and cylindrically shaped, the biotelemetry device being integrated in a capsule in which the radio antenna is placed so that the first face of the substrate faces the inside of the capsule and the second face faces the outside of the capsule.

The characteristics of the various embodiments of the biotelemetry device according to the second aspect can be combined with one another.

The present description relates, according to a third aspect, to an antenna array comprising two antennas according to the first aspect, the two antennas being arranged symmetrically with respect to one another and supplied by the same power supply line. The characteristics, properties, advantages and/or effects of the radio antenna according to the first aspect can be directly transposed to the antenna array according to the third aspect.

BRIEF DESCRIPTION OF THE FIGS.

Other advantages and characteristics of the technique presented above will appear on reading the detailed description below, made with reference to FIGS. in which:

FIG. 1 schematically represents a biotelemetry device according to an exemplary embodiment;

FIG. 2 schematically represents a radio antenna according to an exemplary embodiment;

FIG. 3 schematically represents an antenna array comprising several radioelectric elements according to an exemplary embodiment;

FIG. 4 schematically represents a biotelemetry device according to an exemplary embodiment;

In the various embodiments which will be described with reference to FIGS., similar or identical elements have the same references.

DETAILED DESCRIPTION

The various embodiments and aspects described below can be combined or simplified in many ways. Only certain embodiments of examples are described in detail to ensure the clarity of the description, but these examples are not intended to limit the general scope of the principles emerging from this description considered as a whole.

Figure 1:
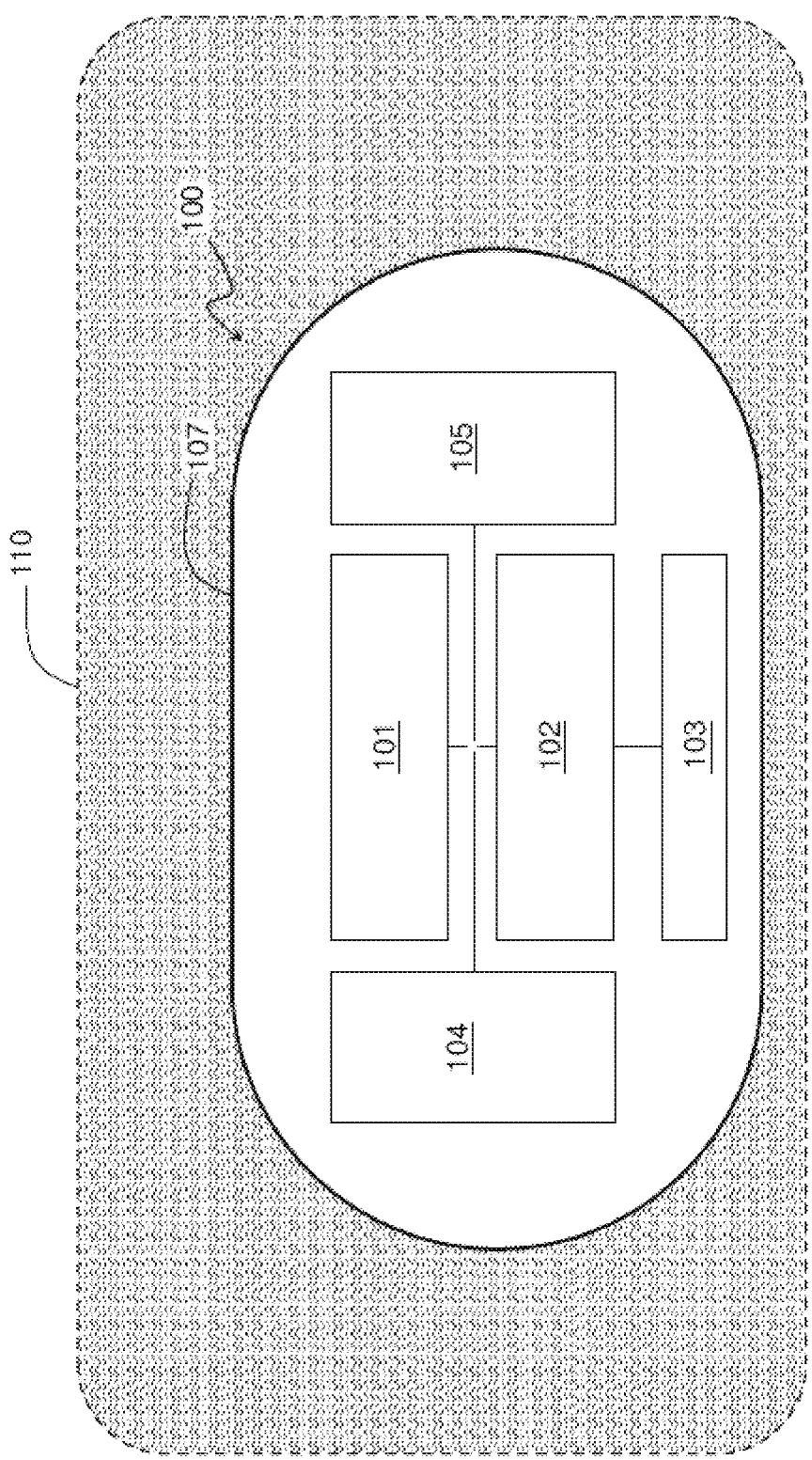

FIG. 1 schematically represents an example of a biotelemetry device 100, in the form of an implantable and/or ingestible capsule.

The biotelemetry device 100 comprises a microcontroller 101, a radio frequency circuit 102, a radio antenna 103, a power source 104. Optionally, the biotelemetry device 100 may include an additional circuit 105, for example a biomedical application circuit or a sensor.

In one or more embodiments, the power source 104 is configured to electrically power the microcontroller 101, the radio frequency circuit 102, the radio antenna 103 and the additional circuit 105.

In one or more embodiments, the radio antenna 103 is configured to communicate via a radio link with an external device (not shown), the radio antenna 103 can for example transmit data (for example biotelemetry data acquired by the biotelemetry device 100) to the external device and receive data (for example operational instructions and/or therapeutic treatment) from such an external device.

In one or more embodiments, the radio antenna can transmit and receive high frequencies electromagnetic waves, for example in the range from $10^8$ Hz to $10^{10}$ Hz.

According to one or more embodiments, the microcontroller comprises an electrical signal generation unit 112 configured to generate the incident electrical signal. According to one or more embodiments, the microcontroller comprises a data processing unit 113.

In one or more embodiments, the microcontroller 101 is configured to generate an incident electrical signal to be converted into an electromagnetic wave by the radio antenna and/or to amplify a signal received from the radio antenna.

In one or more embodiments, the microcontroller 101 is configured to process data, for example to process the data received by the radio antenna 103 or data acquired by the additional circuit 105.

In one or more embodiments, all of the components of the biotelemetry device 100 (the microcontroller 101, the radio frequency circuit 102, the radio antenna 103, the power source 104 and optionally, the an additional circuit 105) is integrated in a biocompatible capsule 107.

In one or more embodiments, the radio frequency circuit 102 is interconnected between the microcontroller 101 and the radio antenna 103. The radio frequency circuit 102 serves as an electrical interface between the microcontroller 101 and the radio antenna 103.

In one or more embodiments, the biomedical application circuit 105 is configured to implement diagnostic functions and/or therapeutic functions. The diagnostic functions may include functions for acquiring or measuring diagnostic data, for example by means of one or more sensors, such as for example, temperature sensors, electronic sensors, MEMS ("Microelectromechanical Systems") or microfluidics sensors. Diagnostic functions may include endoscopy, image acquisition, glucose or other physiological parameters measuring, antibody detection, etc. Therapeutic functions may include, for example, drug delivery and electrical stimulation, such as cardiac or neural stimulation.

The biotelemetry device 100 is intended to be used in a surrounding medium 110, for example after ingestion or in vivo implantation. As the biotelemetry device 100 moves through the human body, for example during gastrointestinal transit, this surrounding medium 110 is likely to have various properties.

The electromagnetic (EM) properties of the surrounding medium 110 surrounding the biotelemetry device 100 determine the coupling between the radio antenna 103 and the surrounding medium 110 and the absorption of EM fields by this surrounding medium 110. Knowing these EM properties makes it possible to adapt the configuration of the radio antenna 103 to optimize the wireless transmission performance of the radio antenna 103 through the surrounding environment. In particular, when the coupling between the radio antenna 103 and the surrounding medium 110 is high, and the transmission properties of the radio antenna can be affected by variations in the EM properties of the surrounding medium 110 in which the biometric device 100 is.

Figure 2:
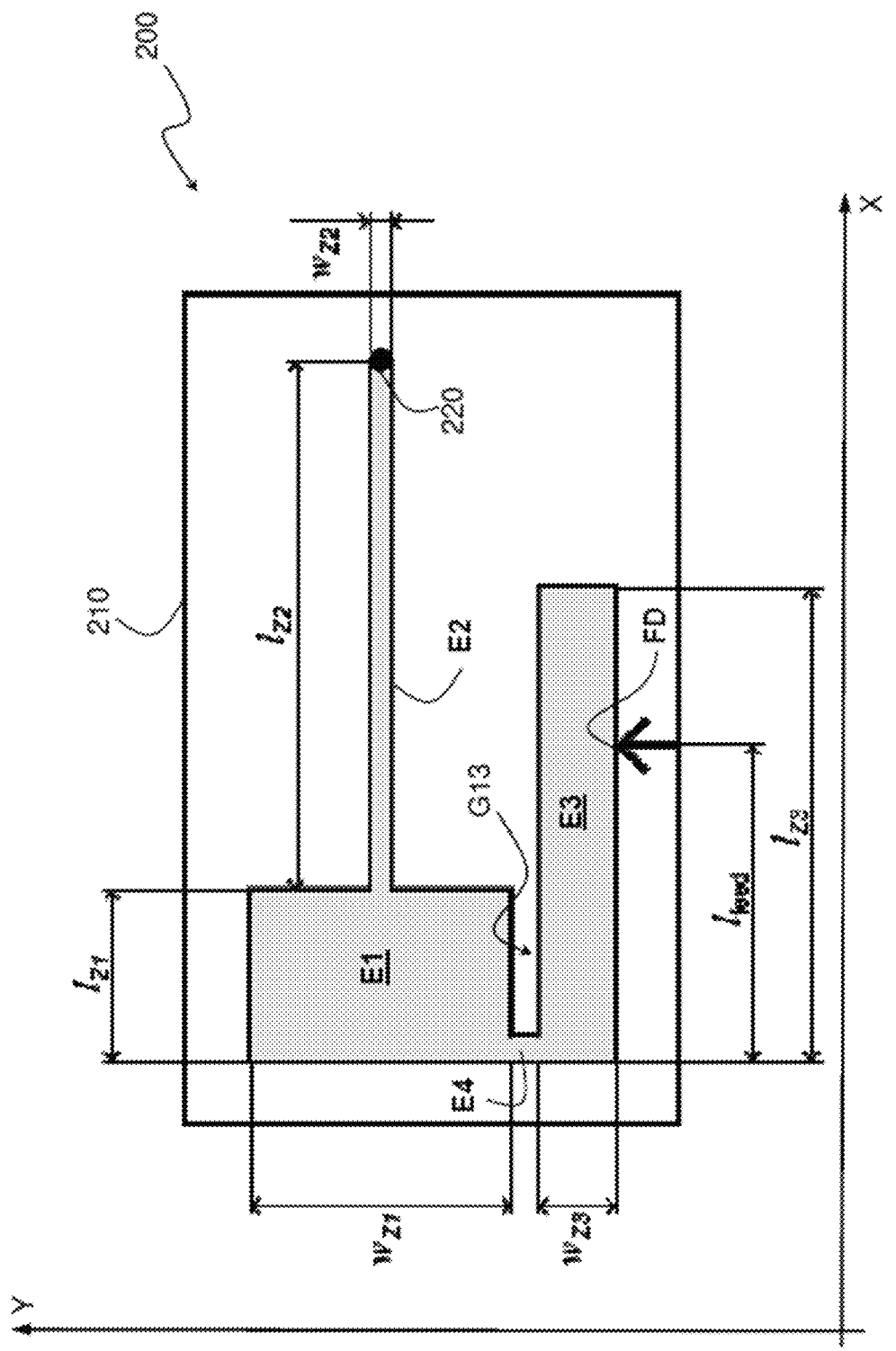

FIG. 2 schematically represents a geometric configuration of a radio antenna 200 adapted for a biotelemetry device 100 such as the one described with reference to FIG. 1, according to an exemplary embodiment.

In one or more embodiments, the components of the radio antenna 200 are integrated into a substrate 210 formed of a dielectric material (for example, FR4, PFTE, polyimide, polyetheretherketone, ceramics, composites, etc.). The substrate 210 is made either of a flexible material and/or which can be rolled, so as to be able to conform to the interior surface of a biotelemetry device such as a capsule, or of a rigid material suitable for the realization of a planar biotelemetry device. The substrate is for example made of flexible polyimide: such a material is capable of conforming to the internal surface of a capsule of a biotelemetry device.

In one or more embodiments, a ground plane is arranged on a first face F2 (below) of the substrate. The ground plane is for example made of an electrically conductive material (for example, metal such as copper, aluminum, silver etc. or an alloy).

In one or more embodiments, the radio antenna 200 comprises a resonator comprising a first element E11, having a first characteristic impedance Z1, a second element E2, having a second characteristic impedance Z2 and a third element E3, having a third characteristic impedance Z3.

In one or more embodiments, the first element E1 is formed by a strip, made of an electrically conductive material, the strip being arranged on a second face F1 (top) of the substrate opposite to the first face F2. The material of the ground plane may be identical to or different from the material of the strip of electrically conductive material. The strip of conductive material can have different geometric shapes: a parallelepiped shape, for example rectangular as in the example shown in FIG. 2, or another form (for example, coiled, meander-patterned, zigzag, etc.) so as to obtain the desired electrical length and impedance, in particular the impedance required to satisfy the equations eq1a and eq1b below.

In one or more embodiments, the second element E2 is formed by a strip, made of an electrically conductive material, the strip being arranged on the second face F1. The strip of conductive material can have different geometric shapes: a parallelepiped shape, for example rectangular as in the example shown in FIG. 2, or another form (for example, coiled, meander-patterned, zigzag, etc.) so as to obtain the electrical length and impedance necessary to satisfy the equations eq1a and eq1b below.

In one or more embodiments, the third element E3 is formed by a strip, made of an electrically conductive material, the strip being arranged on the second face F1. The strip of conductive material can have different geometric shapes: a parallelepiped shape, for example rectangular as in the example shown in FIG. 2, or another form (for example, coiled, meander-patterned or zigzag, etc.) so as to obtain the electrical length which substantially satisfies the equation eq4 below.

The three elements E1, E2, E3 can be made of the same electrically conductive material or of different electrically conductive materials. The materials that can be used are for example copper, aluminum, silver, an alloy, etc.

In one or more embodiments, the third element E3 is configured to receive an incident electrical signal generated by the microcontroller. A connection point FD of a power supply line is provided on the third element E3. Power can be supplied by microstrip or coaxial cable. In one or more embodiments, the electrical supply point FD is located on an external edge of the strip forming the third element, this external edge being opposite the side of the third strip connected to the first element E1 (see example in FIG. 2).

In one or more embodiments, the second element E2 is electrically connected to the ground plane, at a first end of the strip forming the second element, by means of a via 220 passing through the substrate.

In one or more embodiments, the second element E2 forms an extension of the first element E1 and is electrically directly connected to the first element E1 at a second end of the second strip opposite the first end at which is located via 220. The first element E1 is thus electrically connected to the ground plane by successively via 220 and the second element E2.

In one or more embodiments, the first element E1 is separated from the third element E3 by a slot G13. In one or more embodiments, the slot G13 is a rectilinear slot, of fixed width.

In one or more embodiments, the first element E1 is electrically connected to the third element E3 at one end of the first strip forming the first element E1 and one end of the third strip forming the third element E3, through a transition band E4 made of an electrically conductive material closing the slot G13 at one of its ends. The third element E3 is thus electrically connected to the ground plane by successively via 220, the second element E2, the first element E1 and the transition strip E4.

In one or more embodiments, corresponding to the example illustrated in FIG. 2, the second strip forming the second element E2 and the third strip forming the third element E3 extend longitudinally in a first direction (axis X in FIG. 2) and the first strip forming the first element E1 extends longitudinally in a second direction (axis Y in FIG. 2), distinct from the first direction. In one or more embodiments, corresponding to the example illustrated in FIG. 2, the first direction is perpendicular to the second direction or substantially perpendicular to the second direction. In one or more embodiments, the first direction makes an angle between 0° and 45° with the second direction.

In one or more embodiments, the resonator has at least two resonant frequencies. In one or more embodiments, the resonator is configured to convert the incident electrical signal received by the third element E3 into an electromagnetic wave at a frequency corresponding to one of the resonance frequencies of the resonator. The resonance frequency is the frequency for which the imaginary part of the complex impedance of the antenna is equal to zero: Im $(Z_{ANT})=0$.

The antenna has at least two resonance frequencies and two corresponding frequency bands, which increases the possibilities of use of the antenna. For example, a data transfer can be carried out in a first frequency band and a wireless energy transfer can be carried out in a second frequency band (for example using the "Wireless Power Transfer" (WPT) technique). According to another example, a first frequency band can be used for activating the device in which this antenna is placed as well as for data transmission, the second band being suitable for data transmission at the same time as for the transmission of data redundant with the one transmitted via the first band so as to be able to verify the integrity of the data transmitted via the first band and thus increase the reliability of the transmission. By combining in the same multi-band antenna the function of data transmission and energy transfer, one can substantially either miniaturize the device in which this antenna is integrated or increase the space available inside this device.

The geometry (in particular, the dimensions of the three elements E1, E2, E3) of the radio antenna satisfying the resonance condition (each resonance frequency corresponding to a frequency for which the imaginary part of the complex impedance of the antenna $Z_{ant}$ is equal to zero: Im $(Z_{ANT}=0)$ can be deduced from the impedance equation of the transmission lines.

The characteristic impedances Z1, Z2, Z3 of the three elements E1, E2, E3 are respectively functions of the dimensions of these 3 elements. With reference to FIG. 2, we note:

$w_{Z_1}$ the dimension along the Y axis of the first element E1;
$w_{Z_2}$ the dimension along the Y axis of the second element E2;
$w_{Z_3}$ the dimension along the Y axis of the third element E3;
$w_{Z_4}$ the dimension along the Y axis of the slot G13 and of the transition strip E4;
$l_{Z_1}$ the dimension along the X axis of the first element E1;
$l_{Z_2}$ the dimension along the X axis of the second element E2;
$l_{Z_3}$ the dimension along the X axis of the third element E3;
and $l_{feed}$ the position, relative to the end of the third element E3 (origin point of the antenna), of the connection point of the power supply line on the external edge of the third strip.

In one or more embodiments, the first element and the second element are configured to resonate at a first resonance frequency and the third element is configured to resonate at a second resonance frequency greater than the first resonant frequency.

In one or more embodiments, the elements E1 and E2 function as a quarter-wave stepped impedance resonator (SIR) with a transition of impedance (i e jump of impedance) between the element E1 at lower impedance Z1 and the element E2 at higher impedance Z2. In addition, a short circuit (via 220) to the ground plane is made at the end of the element E2 with higher impedance (high impedance end). This implies a distribution of electric current in the elements having its minimum at the end of the element E1 at low impedance Z1 (low impedance end) and its maximum at the end of the element E2 at high impedance Z2 (high end impedance). The voltage distribution is opposite to that of the current.

The characteristic impedances Z1 and Z2 determine the lowest resonant frequency f1. This first resonant frequency f1 depends mainly on the characteristic impedances Z1, Z2 of the first and second elements E1, E2 and is proportional to the ratio of these characteristic impedances Z1/Z2, while the real part of the antenna impedance at this first resonant frequency depends on the characteristic impedances Z1, Z2 of the first and second elements E1 and E2 and is proportional to the product of these characteristic impedances Z1×Z2.

By varying the ratio of the dimensions $w_{Z_1}$ and $w_{Z_2}$ of the elements E1, E2 while keeping the total length of the antenna $l=l_{Z_1}+l_{Z_2}$ fixed, the first resonant frequency f1 can be adjusted to a desired value (with an infinite number of possibilities for Z1, Z2, $l_{Z_1}$ and $l_{Z_2}$) as well as the desired antenna impedance at this first resonance frequency (for example 50 ohms). The ratio $$\frac{w_{Z_1}}{w_{Z_2}}$$

can for example vary between 2:1 and 100:1.

Thus, it is possible to adjust the first resonance frequency f1 by appropriately choosing the dimensions along the Y axis of the first and second bands, then varying the dimensions $w_{Z_1}$, $w_{Z_2}$ according to the X axis of the first and second bands, while keeping constant the total length of the antenna, equal to the sum of the dimensions $l_{Z_1}$, $l_{Z_2}$ according to the X axis of the first and second bands, so as to obtain an impedance adapted to the first frequency of desired resonance.

The first resonance frequency f1 is connected to the dimensions along the Y axis of the first and second bands by the following relationships:

$$Z_1 + Z_2 \tan(\beta_{Z2} l_{Z2}) \tan(\beta_{Z1} l_{Z1}) = 0 \quad \text{(eq 1a)}$$

$$Z_2 \tan(\beta_{Z1} l_{Z1}) + Z_1 \tan(\beta_{Z2} l_{Z2}) \neq 0 \quad \text{(eq 1b)}$$

$\beta_{Z1}$ being the phase constant of the first element E1 defined by:

$$\beta_{Z1} = \frac{2\pi}{c} f_1 \sqrt{\varepsilon_1^{r,\text{eff}}} \quad \text{(eq 2)}$$

where $\beta_{Z2}$ is the phase constant of the second element E2 defined by:

$$\beta_{Z2} = \frac{2\pi}{c} f_1 \sqrt{\varepsilon_2^{r,\text{eff}}} \quad \text{(eq 3)}$$

c being the speed of light, $\varepsilon_2^{r,\text{eff}}$ being the effective relative permittivity of the surrounding medium around the second element, $\varepsilon_1^{r,\text{eff}}$ being the effective relative permittivity of the surrounding medium around the first element.

In one or more embodiments, the element E3 radiates like a half-wave patch antenna. This implies a sinusoidal electrical current distribution, having its minimum at the ends (along the X axis) of the element E3 and its maximum in the middle of the element E3. The voltage distribution is sinusoidal with maxima at the ends (along the X axis) of the element E3 and its minimum in the middle of the element E3. The element E3 determines the other higher resonant frequencies, in particular the second resonant frequency f2. The impedance Z3 of this element can therefore be chosen as a function of the second resonant frequency f2 targeted.

The second resonant frequency f2 mainly depends on the dimension along the X axis of the third element E3:

$$l_{Z3} \approx [2 \times f2(\varepsilon^{\text{eff}})^{0.5}]^{-1} \quad \text{(eq 4)}$$

$\varepsilon^{\text{eff}}$ being the effective permittivity of the surrounding medium around the element E3. The impedance of the $Z_{ANT}$ antenna at this second resonance frequency depends mainly on the dimension along the Y axis of the third band $w_{Z_3}$ and on the position $l_{feed}$ of the connection point of the power supply line on the outer edge of the third strip. The impedance of the $Z_{ANT}$ antenna at this second frequency is in particular proportional to the ratio $$\frac{1}{w_{Z_3}}.$$

Thus, it is possible to adjust the second resonance frequency f2 to a desired value and at the same time obtain an impedance suitable for this second resonance frequency.

In one or more embodiments, a dielectric structure (called superstrate) with low losses and high permittivity contributes to increasing the effective permittivity $\varepsilon^{\text{eff}}$ (see equation eq4 above) and to decoupling the antenna from the medium surrounding at a loss. In one or more embodiments, the dielectric superstrate is disposed above the elements E1, E2 and E3.

One can for example make a radio antenna having the resonance frequencies f1=434 MHz and f2=2.45 GHz, with $w_{Z_1}$=6.7 mm, $zw_{Z_2}$=140 μm, $w_{Z_3}$=550 μm, $w_4$=200 μm, $l_{Z_1}$=4.5 mm, $l_{Z_2}$=13.5 mm, $l_{Z_3}$=8 mm, $l_{feed}$=6 mm, a 102 μm thick PEEK substrate, a 1 mm thick superstrate with the relative permittivity $\varepsilon_r$=80, the 3 elements E1, E2, E3 and the transition band E4 being produced by a copper microstrip 9 μm thick. It has been shown that such a radio antenna has impedance immunity in the two ISM bands (industrial, scientific and medical) around 434 MHz and 2.45 GHz. For the two resonance frequencies, an impedance adaptation to 50 ohms is obtained.

Figure 3:
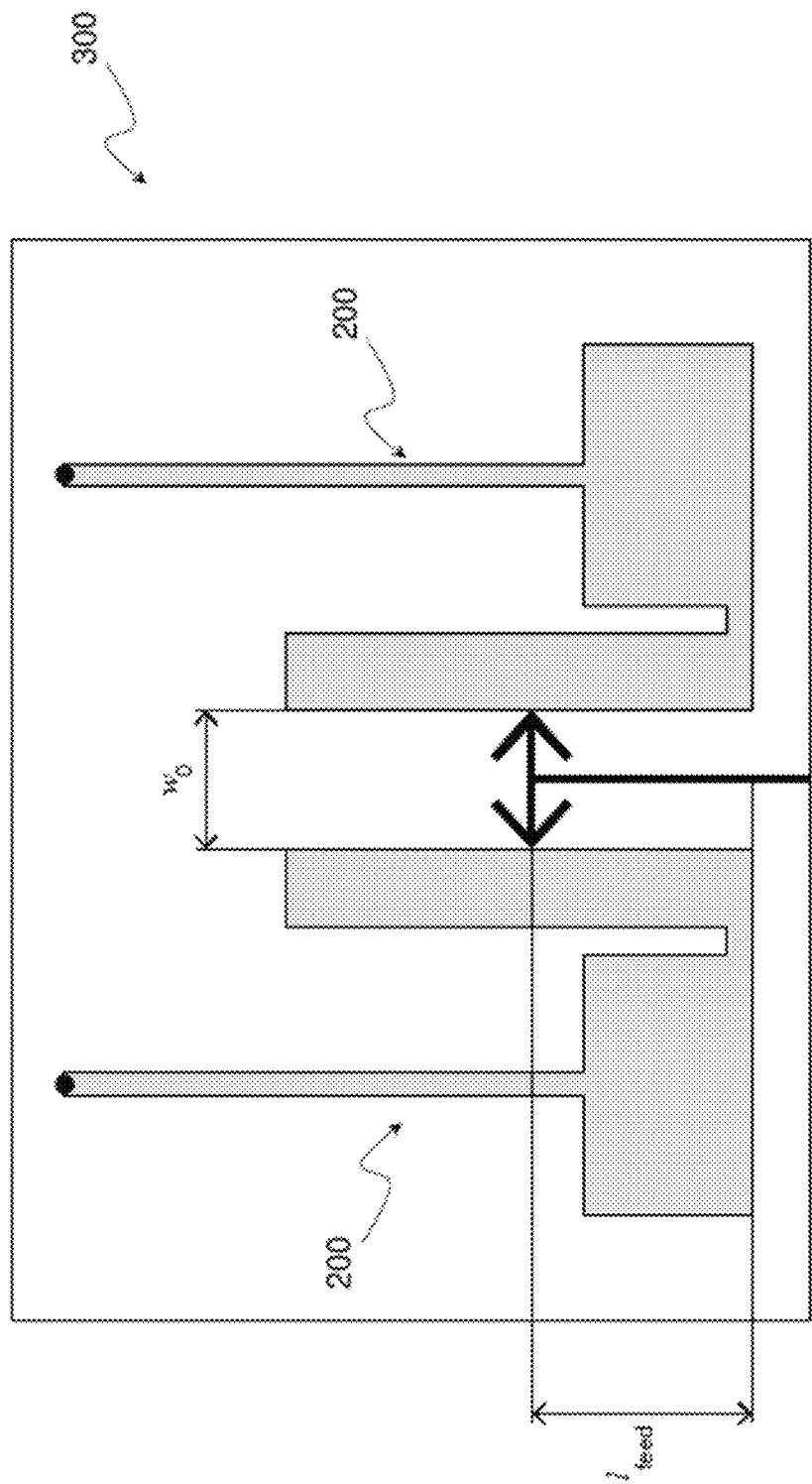

FIG. 3 schematically represents an antenna array 300 comprising two antennas according to the present description on the same substrate, the two antennas being arranged symmetrically with respect to one another and supplied by the same power supply line. In one or more embodiments, the position $L_{feed}$ of the feed point of the two antennas is identical. The two antennas can be identical or slightly different, if one wishes to increase the bandwidth. The network can include two or more antennas supplied by the same power supply line.

When using such an antenna array in a capsule biometric device, the array configuration improves omnidirectionality for the highest resonance frequencies. At the lowest resonant frequency, the omnidirectionality of the antenna is generally good enough. The impedance adaptation with respect to the components of the biotelemetry device (microprocessor and radio frequency circuit in particular) is carried out by adjusting the distance W0 between the elements E3 of each antenna and by adjusting the position $L_{feed}$ of the feed point.

Figure 7A:
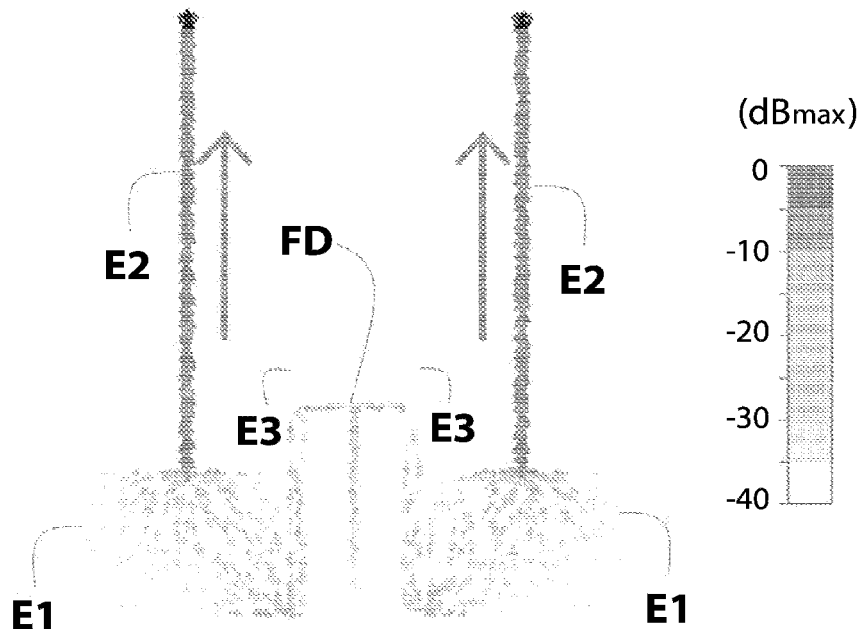
FIGS. 7A and 7B illustrate aspects of the operation and performance of a radio antenna according to an exemplary embodiment.
Figure 7B:
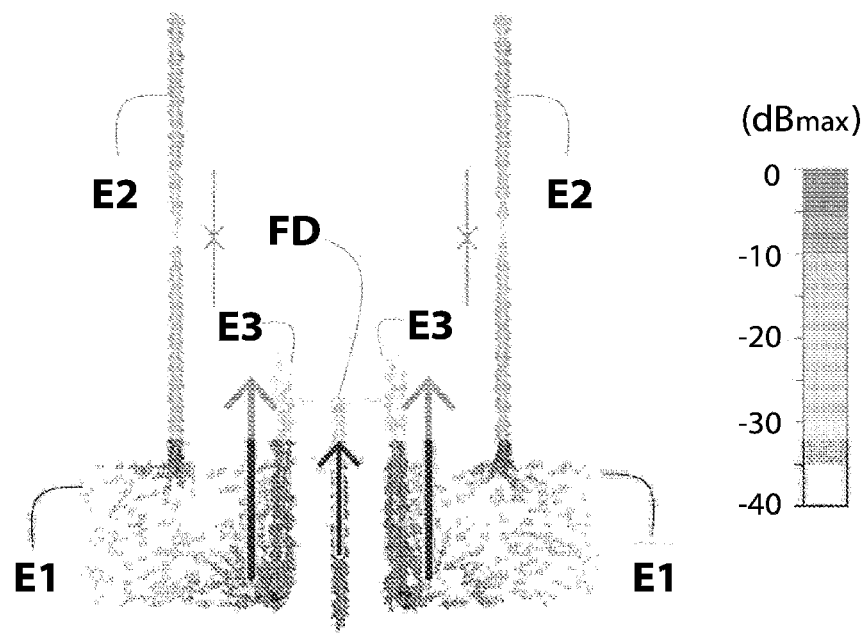

FIGS. 7A and 7B show an example of current distribution which can be obtained at resonance frequencies f1=434 MHz (FIG. 7A) and f2=2.45 GHz (FIG. 7B) respectively with a network of two antennas according to FIG. 3. As explained above, the first element (E1) and the second element (E2) form a quarter wave resonator with impedance jump.

At the frequency f1=434 MHz (FIG. 7A), dominant co-linear currents are observed in the elements E2 with a maximum on the upper edges where the vias 220 connect the element E2 to the ground plane. In this case, the impedance jump from Z1 to Z2 defines the resonance frequency by means of the ratio Zn=Z1/Z2 and electrical lengths $\beta_{Z1} l_{Z1}$ and $\beta_{Z2} l_{Z2}$ (see equation eq1a). The frequency f1 chosen can be obtained for an infinite number of possibilities for Z1, Z2, $L_{Z1}$ and $L_{Z2}$. However, to allow a mode of operation simultaneously at the frequency f2=2.45 GHz induces additional constraints on Z1, Z2, $L_{Z1}$ and $L_{Z2}$.

At the frequency f2=2.45 GHz (FIG. 7B), the wave emitted by the antenna comes mainly from the co-linear currents in the elements E3, with a contribution coming from the supply line FD. Another resonance can also be noted on the element E2: two opposite currents having their maximum intensity at the most distant end of the element E2 meets in the middle (where the minimum of current is obtained). In contrast to what happens at the 434 MHz frequency, the element E1 behaves like a phase inverter at the frequency f2=2.45 GHz. Consequently, the current in the lower half of element E2 is collinear with that in element E3: this contributes substantially to the radiation emitted by the antenna and also impacts the impedance of the antenna, thus contributing to the adaptation of the antenna impedance with respect to the radio frequency circuit.

Figure 4:
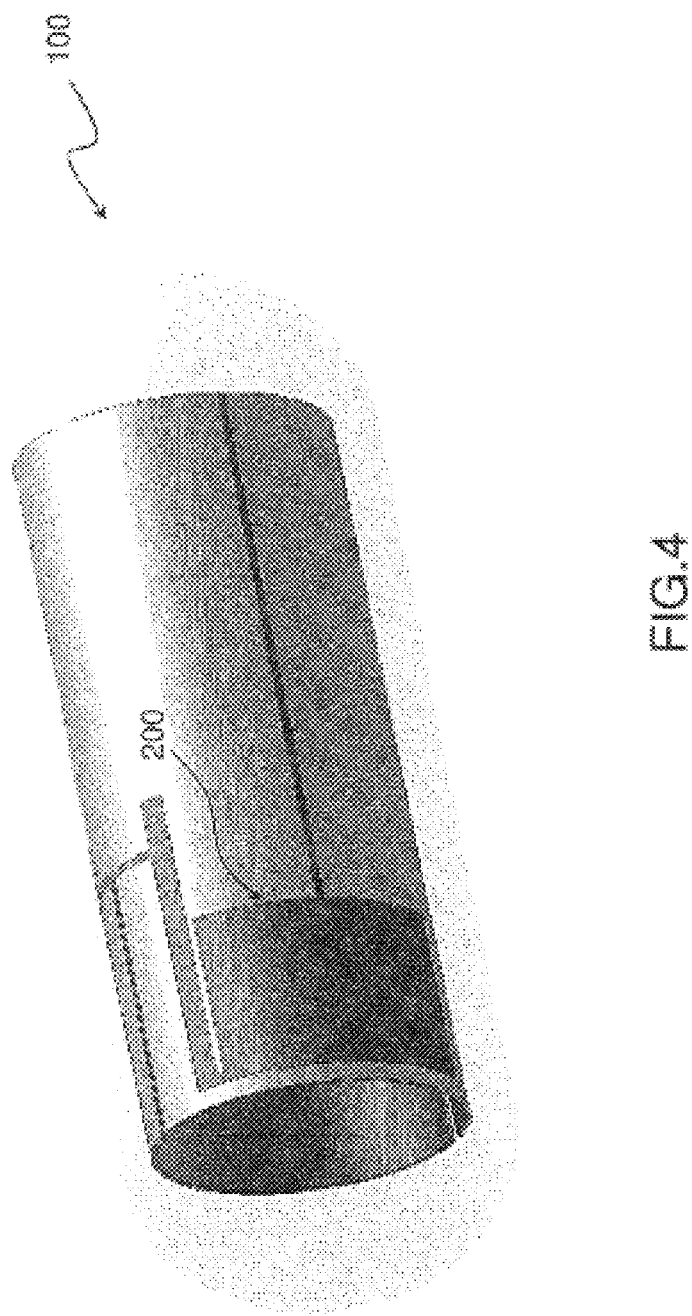

FIG. 4 schematically represents a biotelemetry device 100 comprising at least one radio antenna 200 or an array of antennas 300 according to the present description in an exemplary embodiment.

The biotelemetry device is in the form of a capsule. The capsule can be made of biocompatible plastic material (PVC, PTFE, PEEK, Polyethylene etc.), polymer or ceramic. The capsule is made for example of biocompatible ceramic, the thickness of which is for example 1 mm and the relative permittivity $\varepsilon_r$=80.

In one or more embodiments, the substrate is integrated into the capsule so that the face F2 of the substrate on which the ground plane is arranged faces the interior of the capsule and that the other face F1 on which the three elements E1, E2, E3 are arranged are turned towards the outside of the capsule. The size of the capsule is for example between 15 mm and 50 mm in length and 5 mm to 15 mm in diameter.

In one or more embodiments, the substrate of the radio antenna is a substrate made of flexible material, for example flexible polyimide 102 μm thick conforming to the internal surface of the capsule. The thickness of the substrate mainly affects the impedance bandwidth as for patch antennas, in particular at the lowest resonant frequency F1. More generally, the thickness of the substrate can be between 20 μm and 3 mm.

In one or more embodiments, the substrate is made of a rigid material and of cylindrical shape so as to form a cylindrical radio antenna 200. The dimensions of the substrate and the diameter of the cylinder formed by the substrate are in this case adapted to the internal dimensions of the capsule with the tolerance of 50 μm.

In one or more embodiments, an antenna array with two antennas arranged in a mirror as illustrated in FIG. 3 is produced on the substrate which is then integrated into the biotelemetry device in the form of a capsule. In an exemplary embodiment, the first resonance frequency is 434 MHz and the second resonance frequency is around 2.45 GHz when the antenna array is used in a medium with electromagnetic properties equivalent to muscle tissue.

Figure 5:
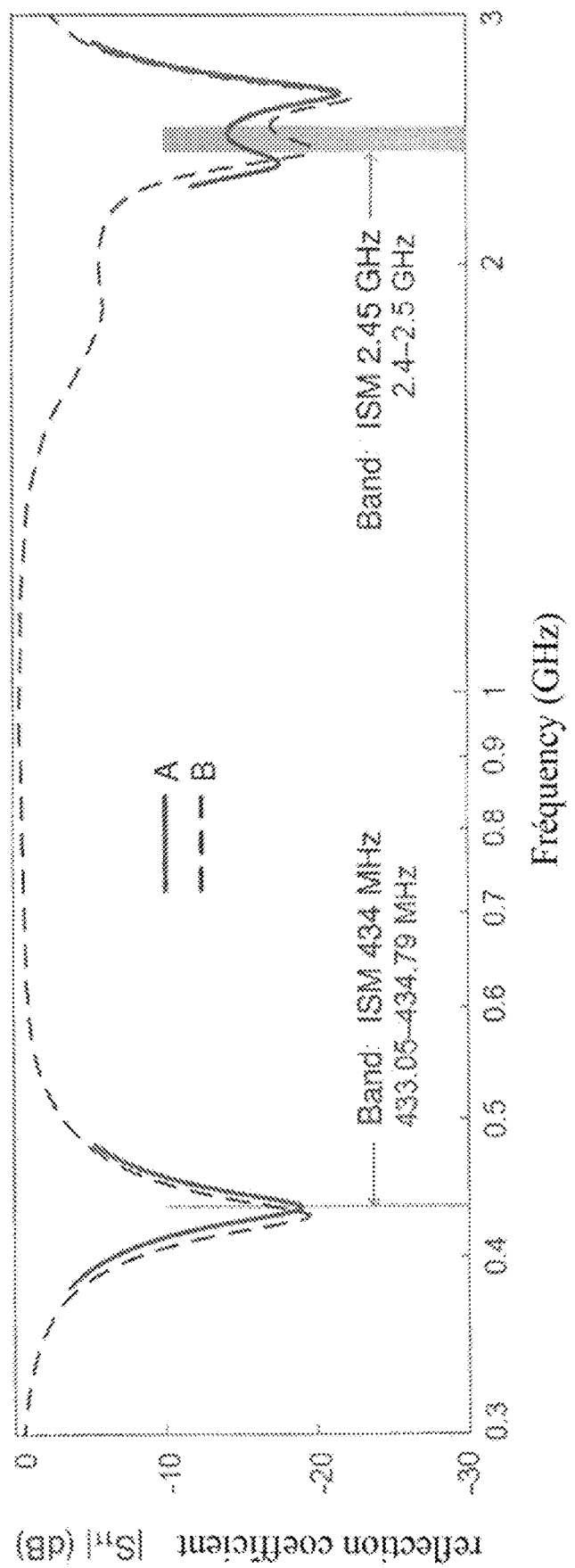
FIG. 5 illustrates aspects of the operation and performance of a radio antenna according to an exemplary embodiment.

FIG. 5 shows the performance of an antenna in terms of impedance according to an exemplary embodiment in which the radio antenna has the properties for the resonance frequencies f1=434 MHz (FIG. 5A) and f2=2.45 GHz (FIG. 5B), with $w_{Z_1}$=6.7 mm, $w_{Z_2}$=140 μm, $w_{Z_3}$=550 μm, $w_{Z_4}$=200 μm, $l_{Z_1}$=4.5 mm, $l_{Z_2}$=13.5 mm, $l_{Z_3}$=8 mm, $l_{feed}$=6 mm, a 102 μm thick PEEK substrate, a 1 mm thick superstrate with the relative permittivity $\varepsilon_r$=80, the 3 elements E1, E2, E3 and the transition band E4 being produced by a copper microstrip 9 μm thick. The curves in FIG. 5 show the variation of the antenna reflection coefficient as a function of the operating frequency. Curves A and B were obtained respectively by two separate methods. The gain achieved is −16.1 dBi at 434 MHz and −14.4 dBi at 2.45 GHz.

Figure 6A:
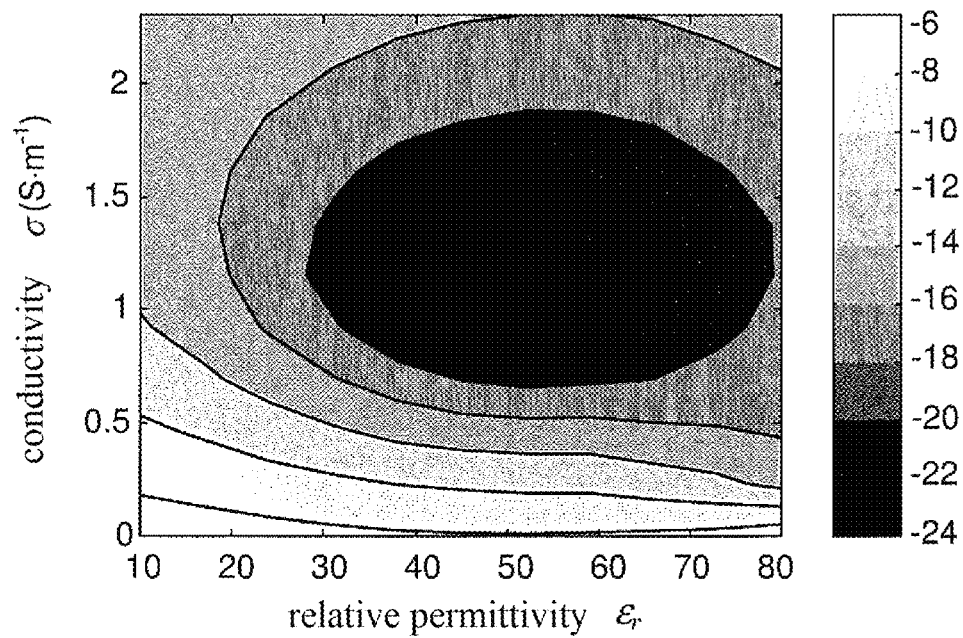
FIGS. 6A and 6B illustrate aspects of the operation and performance of a radio antenna according to another exemplary embodiment.
Figure 6B:
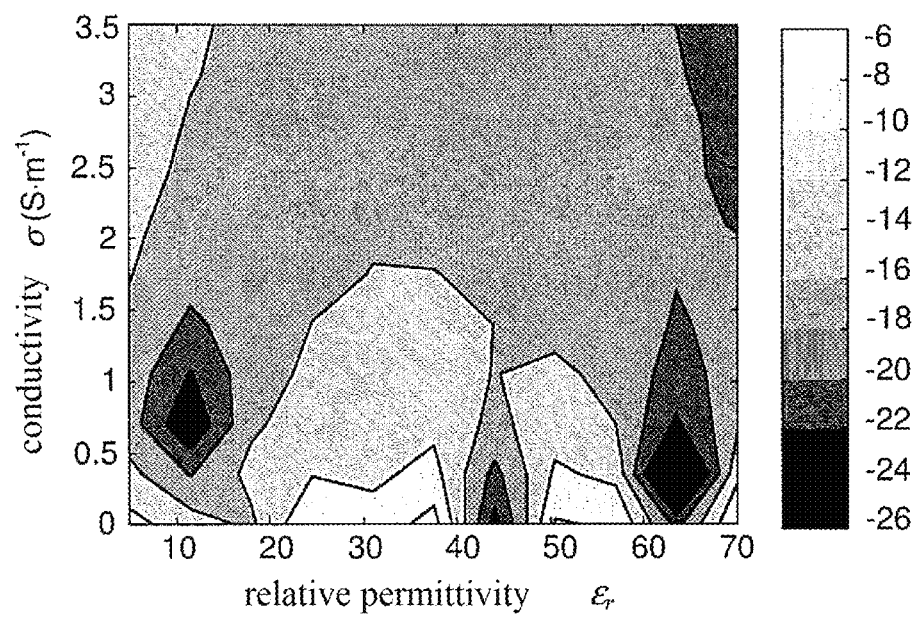

FIGS. 6A-6B show variation curves of the reflection coefficient $|S_{11}|$ as a function of the conductivity and the relative permittivity obtained for the same antenna as that of FIGS. 5A and 5B for the resonance frequencies f1=434 MHz (FIG. 6A) and f2=2.45 GHz (FIG. 6B). These FIGS. 6A-6B show the robustness of the antenna and its ability to operate in a wide variety of environments (conductivity between 0 and 2.5 S/m and relative permittivity between 10 and 80) while retaining a reflection coefficient below—10 dB for all these environments. These media can in particular be human tissue.

The radio antenna described in this document can be designed to operate in a wide range of resonant frequencies, for example between $10^8$ Hz and $6 \times 10^{10}$ Hz. Such an antenna which is robust to variations in the different EM properties of the surrounding medium can be used in any body tissue for multiple application scenarios and has numerous application possibilities whether in the medical or non-medical field, for example, for civil engineering, agriculture, food processing, etc.

One application is its use in an ingestible and/or in vivo implantable biotelemetry device for biotelemetry and teletherapy applications in the human and/or animal body. Another emerging application is that of wireless devices for bidirectional neural interfacing.

The invention claimed is:

1. A multi-band radio antenna, wherein the radio antenna comprises
   a substrate formed of a dielectric material;
   a ground plane of electrically conductive material, arranged on a first face of the substrate;
   a resonator configured to convert an incident electrical signal into an electromagnetic wave and to resonate at least two distinct resonance frequencies, the resonator comprising at least three elements arranged on a second face of the substrate opposite to the first face;
   wherein
   a first element is formed by a first strip of electrically conductive material;
   a second element is formed by a second strip of electrically conductive material;
   a third element is formed by a third strip of electrically conductive material;
   the second element is electrically connected to the ground plane by means of a via passing through the substrate at a first end of the second strip;
   the second element forms an extension of the first element and is electrically connected directly to the first element at a second end of the second strip opposite to the first end;
   the first element is separated from the third element by a slot and electrically connected to the third element at one end of the first strip and one end of the third strip by means of a transition strip of electrically conductive material passing through the slot; and
   the third element is connected to an electrical supply line to receive the incident electrical signal.

2. The antenna according to claim 1, in which: the first element and the second element form a quarter-wave resonator with an impedance jump between the first element and the second element having an impedance greater than that of the first element; and the third element radiates like a half-wave patch antenna.

3. The antenna according to claim 2 in which the first element and the second element are configured to resonate at a first resonance frequency and the third element is configured to resonate at a second resonance frequency greater than the first resonance frequency.

4. The antenna according to claim 1 in which the ratio of the width of the first strip to the width of the second strip is from 2:1 to 100:1.

5. The antenna according to claim 1, in which at least one of the first, second, third, and fourth strips has a parallelepiped, coiled, or zigzag shape.

6. The antenna according to claim 1, in which the thickness of the substrate is 20 µm to 5 mm.

7. The antenna according to claim 1, in which the slot is a straight slot and of substantially fixed width.

8. The antenna according to claim 1, further comprising a high permittivity superstrate.

9. The antenna according to claim 8, in which the superstrate is arranged above the first, second and third elements.

10. The antenna according to claim 1, in which the first element extends longitudinally in a second direction Y distinct from a first direction X in which the second element extends longitudinally; the first and the second elements form a quarter-wave resonator with an impedance jump between the first element and the second element having an impedance greater than that of the first element; and a resonance frequency f1 of the impedance jump resonator is related to the dimensions $l_{Z1}$ and $l_{z2}$ in the second direction Y of the first and second strips by the following equations:

$$Z_1 + Z_2 \tan(\beta_{Z2} l_{Z2}) \tan(\beta_{Z1} l_{Z1}) = 0$$

$$Z_2 \tan(\beta_{Z1} l_{Z1}) + Z_1 \tan(\beta_{Z2} l_{Z2}) \neq 0$$

where $Z_1$ is the impedance of the first element,
$Z_2$ is the impedance of the second element,
$\beta_{Z1}$ is the phase constant of the first element defined by:

$$\beta_{Z1} = \frac{2\pi}{c} f_1 \sqrt{\varepsilon_1^{r,eff}},$$

$\beta_{Z2}$ is the phase constant of the second element defined by:

$$\beta_{Z2} = \frac{2\pi}{c} f_1 \sqrt{\varepsilon_2^{r,eff}},$$

c being the speed of light,
$\varepsilon_2^{r,eff}$ being the effective relative permittivity of the surrounding medium around the second element,
$\varepsilon_1^{r,eff}$ being the effective relative permittivity of the surrounding medium around the first element.

11. An antenna array comprising two antennas according to claim 1, the two antennas being arranged symmetrically with respect to each other and supplied by the same power supply line.

12. A biotelemetry device comprising the radio antenna according to claim 1.

13. The biotelemetry device according to claim 12, the substrate being in a flexible material and the biotelemetry device being in the form of a capsule in which the substrate is rolled so that the first face of the substrate faces the interior of the capsule and the second face faces the outside of the capsule.

14. The biotelemetry device according to claim 13, in which the substrate of the radio antenna is a flexible polyimide substrate conforming to the internal surface of the capsule.

15. The biotelemetry device according to claim 12, in which the substrate is made of a rigid material and cylindrically shaped, the biotelemetry device being integrated in a capsule in which the radio antenna is placed so that the first face of the substrate is faces the interior of the capsule and the second face faces the outside of the capsule.

* * * * *